United States Patent [19]

Noyori et al.

[11] Patent Number: 4,886,903

[45] Date of Patent: Dec. 12, 1989

[54] PROCESS FOR PRODUCTION OF PROSTAGLANDINS D2

[75] Inventors: Ryoji Noyori, Aichi; Masaaki Suzuki, Nogoya; Akira Yanagisawa, Nagoya; Seizi Kurozumi, Kokubunji, all of Japan

[73] Assignee: Teijin Limited, Osaka, Japan

[21] Appl. No.: 244,644

[22] Filed: Sep. 13, 1988

Related U.S. Application Data

[63] Continuation of Ser. No. 746,678, filed as PCT JP84/00470 on Oct. 5, 1984, published as WO85/01728 on Apr. 25, 1985, abandoned.

[30] Foreign Application Priority Data

Oct. 7, 1983 [JP] Japan .............................. 58-187133

[51] Int. Cl.$^4$ ............................................. C07C 177/00
[52] U.S. Cl. ....................................... 560/121; 562/503
[58] Field of Search ........................... 560/121; 562/43

[56] References Cited

U.S. PATENT DOCUMENTS 4,013,695 3/1977 Lin ....................................... 560/121
4,346,228 8/1982 Skuballa et al. ..................... 560/121

FOREIGN PATENT DOCUMENTS 42364 3/1984 Japan .................................. 560/121
122463 7/1984 Japan .................................. 549/365

OTHER PUBLICATIONS

Burton et al., J. C. S. Perkins I, p. 1718 (1977).
Lin et al., J. Org. Chem. 47, 615 (1982).
Suzuki et al., "Synthesis of Prostaglandins D$_1$ and D$_2$ Via the 3-Component Coupling Process", 25 Tetrahedron Letters 1383–1386 (1984).

*Primary Examiner*—Robert Gerstl
*Attorney, Agent, or Firm*—Sughrue, Mion, Zinn, Macpeak & Seas

[57] ABSTRACT

The present invention provides a process for the production of PGD$_2$, wherein 7-hydroxy prostaglandin F$_2\alpha$ is treated with thiocarbonyl diimidazole or its analog and subjecting thus treated product to the reaction to deoxidize the hydroxyl group at the 7-position, the reaction to convert the hydroxyl group to a protecting group, and the reaction to oxidize the hydroxyl group at the 11-position, thus giving PGD$_2$ at a high efficiency.

9 Claims, No Drawings

PROCESS FOR PRODUCTION OF PROSTAGLANDINS D2

This is a continuation of application Ser. No. 746,678 filed as PCT JP84/00470 on Oct. 5, 1984, published as WC85/01728 on Apr. 25, 1985, now abandoned.

TECHNICAL FIELD

The present invention relates to a novel process for the production of prostaglandins $D_2$ (hereinafter prostaglandin may be referred to as PG for short in some cases). More particularly this invention relates to a novel process which comprises treating 7-hydroxy $PGF_2\alpha$ with thiocarbonyl diimidazole or its analog, subjecting thus treated product to the reaction to deoxidize the hydroxyl group at the 7-position, the reaction to convert the hydroxyl group to a protecting group, and the reaction to oxidize the hydroxyl group at the 11-position, thus completing the derivation of $PGD_2$.

BACKGROUND ART

Among the primary prostaglandins, $PGD_2$ is a compound which shows strong biological activities like $PGE_2$ and $PGF_2\alpha$. For example, it has been found of late that $PGD_2$ has useful activities including an antitumor activity (Japanese Patent Application Laid-open No. 124718/'83) and a somnifacient activity (R. Ueno et al., Proc. Nat. Acad. Sci., U.S.A., 80, 1735 (1983)) in addition to a platelet aggregation inhibiting activity (G. L. Bundy et al., J. Med. Chem., 26, 790 (1983)) like $PGE_2$ and $PGI_2$, and accordingly $PGD_2$ is expected to introduce itself as an antitumor agent and a remedy for central nervous system disorder of a new medicinal type.

Several methods as mentioned below have hitherto been known for the production of $PGD_2$.

(1) A method comprising the decomposition of prostaglandin endoperoxide produced by biosynthesis from arachidonic acid (see M. Hamberg et al., Proc. Nat. Acad. Sci., U.S.A., 70, 899 (1973)).

(2) A method in which $PGD_2$ is obtained by oxidizing the 11-position of prostaglandin $F_2\alpha$ whose hydroxyl group at the 15-position is protected (see M. Hayashi et al., J. Org. Chem., 38, 2115 (1973)); E. E. Nishizawa et al., Prostaglandins, 9, 109 (1975)).

(3) A method in which $PGD_2$ is obtained by oxidizing the hydroxyl group at the 11-position of prostaglandin $F_2\alpha$ whose hydroxyl groups at the 9- and 15-positions are protected (see D. P. Reynolais et al., Chem. Commun , 1150 (1979); R. F. Newton et al., J. Chem. Soc., Perkins I. 2055 (1981); E. F. Jenny et al., Tetrahedron Letters, 26, 2235 (1974); N. H. Andersen et al , Prostaglandins, 14, 61 (1977).

(4) A method of producing $PGD_2$ by deprotecting the 11-actal body of $PGD_2$ obtained from Corey lactone (see E. W. Collington et al., Tetrahedron Letters, 30, 3125 (1983)).

These methods, however, having their respective drawbacks; for instance, the method (1), in which the desired $PGD_2$ is obtained by means of biosynthesis, may be regarded as very inefficient since this method has not only much difficulty in the handling of PG endoperoxide, the material compound, because of its lability but also much $PGE_2$ formed as by-product in the course of the decomposition reaction. The method (2) is a method in which $PGD_2$ is derived from $PGF_2\alpha$, the material compound which is a drug per se, by means of oxidation which takes place unselectively with the hydroxyl group at the 9- and 11-positions, causing the formation of a lot of by-products and the total yield from the costly material $PGF_2\alpha$ is only 20% at most. The method (3) is to obtain $PGD_2$ from the material $PGF_2\alpha$, whose hydroxyl groups at the 9- and 15-positions are protected, derived from the intermediate formed during the making of $PGF_2\alpha$ through the intricate conversion of functional groups, with the faults that it requires many processes for the production and also that the total yield is low. The method (4) involves a disadvantage of making good use of only one of the produced isomers since the obtained $PGD_2$, whose 11-position is acetalized, is mixed with the stereoisomer having a hydroxyl group at the 15-position.

DISCLOSURE OF THE INVENTION

Taking the abovementioned points into consideration, the inventors of the present invention have conducted a study on the advantageous method for the production of $PGD_2$ and successfully completed a method by which $PGD_2$ is produced from $PGF_2\alpha$ having a protected hydroxyl group at the 9- and 15-positions derived easily from 7-hydroxy $PGF_2\alpha$, which is obtained from 4-hydroxycyclopentenone through two processes, by subjecting it to the reaction in which the hydroxyl group at the 7-position is specifically deoxidized and converting the hydroxyl group to a protecting group, thus achieving this invention.

More particularly, the present invention relates to a process for producing prostaglandin $D_2$ expressed by the following formula (6)

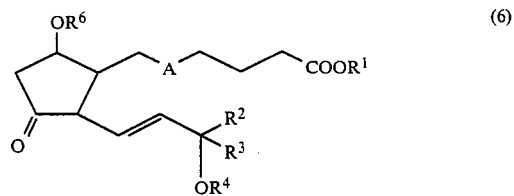

(6)

wherein A indicates a single bond, a double bond, or a triple bond; $R^2$ and $R^3$ are the same or different from each other, each representing a hydrogen atom, a $C_1 \sim C_{10}$ alkyl group which may be substituted or may not be substituted, or a cycloalkyl group which may be substituted or may not be substituted; $R^1$ indicates a hydrogen atom, a $C_1 \sim C_{10}$ alkyl group, a phenyl group which may be substituted or may not be substituted, an alicyclic group which may be substituted or may not be substituted, a phenyl ($C_1 \sim C_2$) alkyl group which may be substituted or may not be substituted, a tri ($C_1 \sim C_7$)hydrocarbon silyl group, or one equivalent of cation; $R^4$ and $R^6$ are the same or different from each other, each representing a hydrogen atom or a group which forms an acetal bond together with an oxygen atom of a hydroxyl group, comprising treating 7-hydroxy prostaglandin $F_2\alpha$ expressed by the following formula (1)

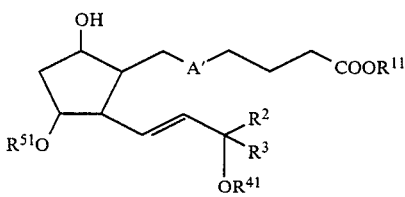
(1)

wherein $R^{11}$ indicates a $C_1 \sim C_{10}$ alkyl group, a phenyl group which may be substituted or may not be substituted, an alicyclic group which may be substituted or may not be substituted, a phenyl ($C_1 \sim C_2$) alkyl group, or a tri($C_1 \sim C_7$)hydrocarbon silyl group; $R^2$ and $R^3$ are as defined hereinabove; $R^{41}$ indicates a group which forms an acetal bond together with an oxygen atom of a hydroxyl group; $R^{51}$ indicates a tri($C_1 \sim C_7$)hydrocarbon silyl group; and A' indicates a triple bond or a double bond, with thiocarbonyl diimidazole or its analog to obtain a thiocarbonate body expressed by the following formula (2)

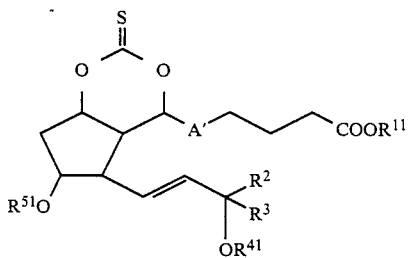
(2)

wherein $R^{11}$, $R^2$, $R^3$, $R^{41}$, $R^{51}$, and A' are as defined hereinabove, which is then subjected to the reaction to deoxidize the hydroxyl group at the 7-position, followed by the reduction of the triple bond or a double bond at the 5-position, if necessary, to give prostaglandin $F_{2\alpha}$ expressed by the following formula (3)

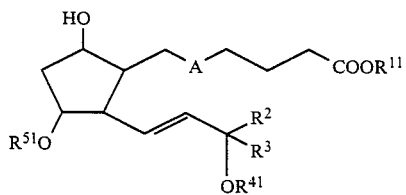
(3)

wherein A indicates a single bond, a double bond, or a triple bond; $R^{11}$, $R^2$, $R^3$, $R^{41}$, and $R^{51}$ are as defined hereinabove, whose hydroxyl group at the 9-position is protected thereafter with a group which forms an acetal bond together with an oxygen atom of the hydroxyl group, followed, if necessary, by reduction of the triple bond or double bond at the 5-position, to obtain protected prostaglandin $F_{2\alpha}$ expressed by the following formula (4)

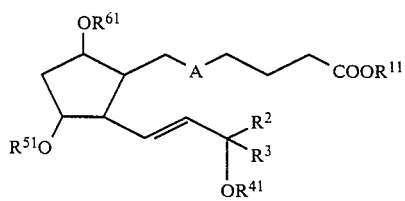
(4)

wherein $R^{61}$ indicates a group which forms an acetal bond together with an oxygen atom of the hydroxyl group; $R^{11}$, $R^2$, $R^3$, $R^{41}$, $R^{51}$, and A are as defined hereinabove, which is then subjected to the selective deprotection reaction, followed, if necessary, by the reduction of the triple bond or the double bond at the 5-position, to obtain prostaglandin $F_{2\alpha}$ expressed by the following formula (5)

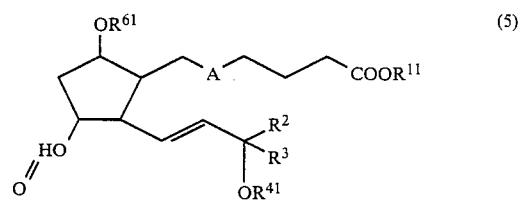
(5)

wherein $R^{11}$, $R^2$, $R^3$, $R^{41}$, and $R^{61}$ are as defined hereinabove, which is then subjected to the oxidation reaction, followed, if necessary, by the reduction of the triple bond or the double bond at the 5-position, deprotection, hydrolysis and/or salt-forming reaction.

7-Hydroxy $PGF_{2\alpha}$, which is the material compound to be used in the method proposed by the present invention, can be obtained by reducing 7-hydroxy $PGE_2$ (European Laid-Open Patent Publication No. 79,733) according to the method of reduction reaction publicly known per se, i.e., by reduction with boron hydroxide sodium diisobutylaluminium 2,6-di-t-butyl-4-methylphenoxide (S. Iguchi et al., Bull., Chem. Soc., Japan, 45, 3033 (1981); G. P. Pollini et al., J. Org. Chem., 45, 3141 (1980); K. G. Untch et al., J. Org. Chem., 44, 3755 (1979)).

In the aforementioned formula (1), $R^{11}$ indicates a $C_1 \sim C_{10}$ alkyl group, a phenyl group which may be substituted or may not be substituted, an alicyclic group which may be substituted or may not be substituted, a phenyl ($C_1 \sim C_2$) alkyl group, or a tri($C_1 \sim C_7$)hydrocarbon silyl group. As the $C_1 \sim C_{10}$ alkyl group, such linear or branched ones as methyl, ethyl, n-propyl, iso-propyl, n-butyl, sec-butyl, tert-butyl, n-pentyl, n-hexyl, n-heptyl, n-octyl, n-nonyl, and n-decyl, for instance, may be mentioned.

The substituent of the phenyl group, which may be substituted or may not be substituted, may include a halogen atom, a hydroxy group, a $C_2 \sim C_7$ acyloxy group, a $C_1 \sim C_4$ alkyl group which may be substituted with a halogen atom, a $C_1 \sim C_4$ alkoxy group which may be substituted with a halogen atom, a nitrile group, a carboxyl group, and a ($C_1 \sim C_6$) alkoxycarbonyl group as desirable ones. Here, as the halogen atom, fluorine, chlorine, and bromine may be mentioned and fluorine and chlorine are especially preferable. As the $C_2 \sim C_7$ acyloxy group, acetoxy, propionyloxy, n-butyryloxy, iso-butyryloxy, n-valeryloxy, iso-veleryloxy, caproyloxy, enanthyloxy, and benzoyloxy, for instance, may be mentioned.

As the $C_1 \sim C_4$ alkyl group which may be substituted with a halogen atom, methyl, ethyl, n-propyl, iso-propyl, n-butyl, chloromethyl, dichloromethyl, and trifluoromethyl may be mentioned as desirable ones. As the $C_1 \sim C_4$ alkoxy group which may be substituted with a halogen atom, methoxy, ethoxy, n-propoxy, iso-propoxy, n-butoxy, chloromethoxy, dichloromethoxy, and trifluoromethoxy, for instance, may be mentioned as desirable ones. As the ($C_1 \sim C_6$) alkoxycarbonyl group, methoxycarbonyl, ethoxycarbonyl, butoxycarbonyl, and hexyloxycarbonyl, for instance, may be mentioned.

The phenyl group may have 1~3 substituents mentioned above, desirably 1 substituent.

As the substituted or unsubstituted alicyclic group, saturated or unsaturated $C_5 \sim C_8$, desirably $C_5 \sim C_6$ groups, which are substituted with the same substituent as described above or not substituted, such as cyclopentyl, cyclohexyl, cyclohexenyl, cycloheptyl, and cyclooctyl may be mentioned.

As the substituted or unsubstituted phenyl ($C_1 \sim C_2$) alkyl group, benzyl, α-phenetyl, and β-phenetyl, in which the phenyl groups are substituted with the same substituent as mentioned above or not substituted, may be mentioned.

As the tri($C_1 \sim C_7$)hydrocarbon silyl group, tri($C_1 \sim C_4$)alkylsilyl such as trimethylsilyl, triethylsilyl, and t-butyldimethylsilyl group; diphenyl($C_1 \sim C_4$)alkylsilyl such as t-butyldiphenylsilyl group; tribenzylsilyl group; and dimethyl-(2,4,6-tri-t-butylphenyloxy)silyl group may be cited as preferable ones.

$R^2$ and $R^3$ are the same or different from each other, each representing a hydrogen atom, or a substituted or unsubstituted $C_1 \sim C_{10}$ alkyl group, or a substituted or unsubstituted 5- to 6-membered cycloalkyl group. As the unsubstituted $C_1 \sim C_{10}$ alkyl group, there are, for instance, such linear or branched ones as methyl, ethyl, n-propyl, iso-propyl, n-butyl, n-pentyl, n-hexyl, 2-methyl-1-hexyl, 2-methyl-2-hexyl, n-heptyl, and n-octyl. As the unsubstituted 5- to 6-membered cycloalkyl group, there are a cyclopentyl group and cyclohexyl group. As the substituent of said unsubstituted $C_1 \sim C_{10}$ alkyl group and unsubstituted 5- to 6-membered cycloalkyl group, those substituents mentioned as the substituents of $R^{11}$ may be cited.

As $R^2$, methyl, n-pentyl, n-hexyl, 2-methyl-1-hexyl, cyclopentyl group and cyclohexyl group that may be substituted by methyl, phenoxy group, or trifluoromethylphenoxy are desirable and of these n-pentyl, n-hexyl, 2-methyl-1-hexyl, cyclopentyl, and cyclohexyl are especially desirable ones. As $R^3$, a hydrogen atom and a methyl group are desirable and a hydrogen atom is especially desirable. $R^{51}$ indicates a tri($C_1 \sim C_7$)hydrocarbon silyl group and as such a tri($C_1 \sim C_7$)hydrocarbon silyl group, the same tri($C_1 \sim C_7$)hydrocarbon silyl groups that are described in detail with regard to $R^{11}$ hereinbefore and, of them all, a t-butyldimethylsilyl group and a triethylsilyl group are desirable. $R^{41}$ indicates a group which forms an acetal bond together with an oxygen atom of a hydroxyl group and as the example of $R^{41}$, methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofranyl, and 6,6-dimethyl-3-oxa-2-oxo-bicyclo(3,1,0)hex-4-yl group may be mentioned. Of these, a 2-tetrahydropyranyl group and a 2-methoxy-2-propyl group are desirable as $R^{41}$.

A' in the aforementioned formula (1) indicates a triple bond or a double bond. As the double bond, a cis-double bond is desirable.

Since prostaglandins expressed by the aforementioned formulae (1) to (5) in the process of the present invention have an asymmetric carbon atom at the 7-, 8-, 9-, 11-, 12- and 15-positions, they have various stereoisomers, and the prostaglandins in the present invention involve their enantiomers, optical isomers, and their mixtures.

The process of this invention initiates a series of reactions with the treatment of 7-hydroxy $PGF_{2\alpha}$ of the aforementioned formula (1) with thiocarbonyl diimidazole or its analog to obtain a thiocarbonate body of formula (2) with its hydroxyl groups at the 7- and 9-positions protected.

Said thiocarbonyl diimidazole is expressed by the following formula.

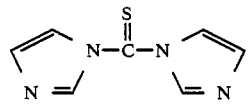

As the analog of thicarbonyl diimidazole, $C_1 \sim C_6$ alkyl groups such as methyl and ethyl; $C_1 \sim C_6$ alkoxy groups such as methoxy, ethoxy, and propoxy; and thiocarbonyl imidazole substituted by halogen atoms such as fluorine and chlorine may be mentioned.

Thiocarbonyl diimidazole or its analog is used in an amount of 1 to 5 equivalents, preferable 1 to 1.5 equivalents, per equivalent of 7-hydroxy $PGF_{2\alpha}$ of formula (1), the starting material. It is advisable to use a base as an reaction auxiliary. As such a base, amines such as 4-dimethylaminopyridine, pyridinetriethylamine, diisopropylcyclohexylamine, and isopropyldimethylamine may be mentioned as desirable ones. The base is used in an amount of 1 to 10 equivalents, most desirably 1.5 to 4 equivalents, per equivalent of the material. A medium is used to make the reaction proceed smoothly Nitriles such as acetonitrile and propionitrile; hydrocarbon halogenides such as carbon tetrachloride, methylene chloride, chloroform, and dichloroethane; and a mixed medium thereof are used as the medium and, of these media, acetonitrile helps to give the best yield. The reaction is carried out at a temperature ranging from 0° C. to 60° C., preferably between 10° C. and 30° C. The end point of the reaction is detected by observing the disappearance of the material by thin-layer chromatography. After the reaction is over, the reaction solution is post-treated according to the ordinary method to give a novel thiocarbonate body of formula (2) with its 7- and 9-position protected as a reaction product. This compound is not only a novel product per se but also expected to display a pharmaceutical activity as a novel prostaglandin when its $R^{41}$ and $R^{51}$ are deprotected.

The obtained thiocarbonate body of formula (2) is then subjected to the reaction to have the hydroxyl group at the 7-position deoxidized. The deoxydizing reaction can be carried out desirably by treating the thiocarbonate body with an organic tin compound expressed by the following formula $(R^7)_3SnH$ wherein $R^7$ indicates a $C_1 \sim C_{10}$ alkyl group or phenyl group, and then by further treating with a base.

As the organic tin compound, trimethyltin hydride, triethyltin hydride, tri-n-butyltin hydride, tri-n-hexyltin hydride, tri-n-octyltin hydride, tri-n-decyltin hydride, triphenyltin hydride, and diphenylmonomethyltin hydride may, for instance, be mentioned. Of all these organic tin compounds, tri-n-butyltin hydride and triphenyltin hydride are desirable ones, and tri-n-butyltin hydride is especially desirable. The organic tin compound is recommendably used under the coexistence with a radical inducing agent. As the radical inducing agent, α,α-azobisisobutyronitrile, bis-tert-butylperoxide, tert-butylhydroperoxide, cumene hydroperoxide, and benzoyl peroxide may, for instance, be mentioned and bis-tert-butylperoxide is especially desirable.

The organic tin compound is used in an amount of 1 to 200 equivalents, desirably 5 to 50 equivalents, per equivalent of the material thiocarbonate body of formula (2).

The radical inducing agent is used in an amount of 1 to 10% by weight of the thiocarbonate composition of formula (2).

The reaction can be conducted in an inert organic medium. As the inert organic medium, aromatic hydrocarbons such as benzene and toluene; aliphatic hydrocarbons such as pentane and hexane; and ethers such as ether and tetrahydrofuran may be mentioned.

The reaction is usually carried out at a temperature ranging from 10° C. to 100° C., preferably at 20° C. to 60° C. The reaction solution is then cooled to somewhere around room temperature (15° C.~25° C.) and treated with a base. As the base, alkoxide-alcohols such as sodium methylate-methanol and sodium ethylate-ethanol are desirable and especially in case where the material compound of formula (2) is methyl ester, bases of sodium methylate-methanol type are used preferably. Its amount is 1 to 50 equivalents, preferably 2 to 5 equivalents, per equivalent of the material compound of formula (2). As the reaction media, such ethers as anhydrous ether, dioxane, and tetrahydrofuran may be used. The reaction is usually conducted around room temperature (15° C.~30° C.) and terminated by confirming the disappearance of the material compound by means of thin-layer chromatography. The reaction is usually completed in 11 to 30 hours. The reaction solution thus obtained is then subjected to after-treatment according to the ordinary method to give PGF$_2$α expressed by the aforementioned formula (3) with the 11- and 15-positions protected.

Thereafter, the triple bond or double bond indicated by A' may be reduced, if necessary. It is desirable to effect such reduction by means of hydrogenation conducted with the use of Lindlar catalyst, synthetic quinoline catalyst of palladium-barium sulfate, or palladium-carbon catalyst.

The hydrogenation reaction is usually conducted in an organic solvent such as benzene and cyclohexane as the desirable method, usually with its reaction time extending over 1 to 15 hours at a reaction temperature standing at room temperature. The triple bond indicated by A' is reduced to a double bond or a single bond and the double bond to a single bond selectively to obtain prostaglandin F$_2$α of formula (3).

The obtained reaction product of formula (3) is then protected with a group which forms an acetal bond together with an oxygen atom of the hydroxyl group. As the protective agent, those, which can form such a protecting group, including 2,3-dihydropyran, 2,3-dihydrofuran, and ethyl vinyl ether, for instance, are used. The protective agent is used in an amount of 1 to 20 equivalents, preferably 1 to 5 equivalents, per 1 equivalent of the material prostaglandin F$_2$α. It is recommendable to use pyridine-para-toluene-sulfonate (PPTS) or camphor-sulfonic acid may be used as the reaction auxiliary in an amount of 0.1 to 100% by weight, preferably 1 to 30% by weight, of the material prostaglandin F$_2$α. The reaction can also be conducted in anhydrous ethers which include, for instance, ethyl ether, tetrahydrofuran, and dioxane, and in anhydrous hydrocarbon halogenides including methylene chloride, chloroform, and dichloroethane. The reaction is carried out at a temperature ranging from $-10°$ C. to 60° C., preferably from 0° C. to 30° C. and the termination of the reaction is confirmed by observing the disappearance of the material compound by thin-layer chromatography. Thereafter, the reaction solution is after-treated by ordinary method to give PGF$_2$α, expressed by the aforementioned formula (4), whose 11-position is protected by a silyl group and 9- and 15-positions protected by a group which forms an acetal bond together with an oxygen atom of the hydroxyl group.

After the reaction with the protective agent is over, the triple bond and the double bond represented by A may be reduced according to the same method of hydrogenation as mentioned above, if necessary.

Then the tri($C_1$~$C_7$)hydrocarbon silyl group at the 11-position of prostaglandin F$_2$α of formula (4) is deprotected. This deprotection can be achieved according to the ordinary method by use of tetra-n-butyl ammonium fluoride or hydrogen fluoride-pyridine, desirably by use of tetra-n-butyl ammonium fluoride.

As the solvent, tetrahydrofuran and diethyl ether dioxane are used. The reaction temperature is usually in the range of $-20°$ C. up to 80° C. and the reaction time is 10 minutes to 24 hours.

After the selective deprotection reaction is over, the triple bond and double bond represented by A may be reduced according to the same hydrogenation as mentioned above, if necessary.

In this way, PGF$_2$α expressed by the following formula (5) with the 9- and 15-positions protected can be readily produced,

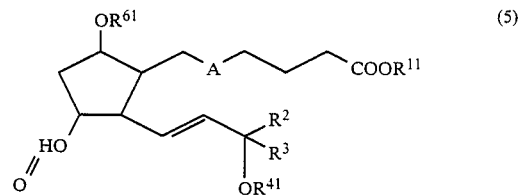

wherein $R^{11}$, $R^2$, $R^3$, $R^{41}$, $R^{51}$, and A are as defined hereinbefore. Thus obtained product can be oxidized according to any method publicly known per se (see E. E. Nishizawa et al., Prostaglandins, 9, 109 (1975); Bundy et al., J. Med. Chem., 26, 740~799 (1983); F. Newton et al., J. Chem. Soc., Perkin I, 2055 (1981); W. Hart et al., J. Chem. Soc. Chem. Comm., 156 (1979)) by use of an oxidizing agent of chromic acid type such as Jones reagent and pyridinium chlorochromate.

As the solvent, hydrocarbon halogenides such as carbon tetrachloride, methylene chloride, chloroform, and dichloroethane; nitriles such as acetonitrile and propionitrile; and aceton, for instance, are used. The reaction temperature usually ranges from $-50°$ C. to room temperature and the reaction time ranges from 10 minutes to 5 hours.

The obtained product may further be subjected to the reduction of the triple bond or the double bond at the 5-position, deprotection, salt-forming reaction and/or hydrolyzing reaction, if necessary.

The reduction of the triple bond or the double bond at the 5-position can be achieved by the same method of hydrogenation as mentioned before.

Deprotection is a known method per se and can be effected, for instance, by treating the product at room temperature in a mixture of acetic acid, water, and tetrahydrofuran (3:1:1~3:2:2) (see E. J. Corey et al., J. Amer. Chem. Soc., 24, 6190 (1972)).

The hydrolyzing reaction, or the reaction in which the ester group ($R^{11}$) at the 1-position is hydrolyzed, is a reaction publicly known per se and can be carried out by use of a hydrolase such as lipase and esterase.

The salt-forming reaction is also a reaction known per se and can be effected by putting the product having a carboxyl group obtained in the aforementioned hydrolyzing reaction into neutralization with sodium hydroxide, potassium hydroxide, sodium carbonate, or a base such as ammonia, trimethylamine, monoethanolamine, and morpholine according to the ordinary method.

Prostaglandin $D_2$ expressed by the following formula (6) is thus obtained:

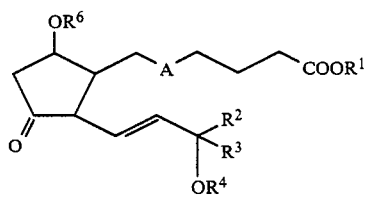

(6)

wherein A, $R^2$, and $R^3$ are as defined hereinabove; $R^1$ indicates a hydrogen atom, a $C_1 \sim C_{10}$ alkyl group, a phenyl group which may be substituted or may not be substituted, an alicyclic group which may be substituted or may not be substituted, a phenyl($C_1 \sim C_2$) alkyl group which may be substituted or may not be substituted, a tri ($C_1 \sim C_7$)hydrocarbon silyl group, or one equivalent of cation; $R^4$ and $R^6$ are the same or different from each other, each representing a hydrogen atom or a group which forms an acetal bond together with an oxygen atom of a hydroxyl group. As the one equivalent of cation represented by $R^1$ in formula (6), alkali metal cations such as $Na^+$ and $K^+$; divalent or trivalent metal cations such as $\frac{1}{2} Ca^{2+}$, $\frac{1}{2} Mg^{2+}$, and $\frac{1}{3} Al^{3+}$; and ammonium cations such as ammonium ion and tetramethylammonium ion may be mentioned.

Examples of $PGD_2$ obtained according to this invention are as follows:
(100) Prostaglandin $D_2$
(102) Prostaglandin $D_1$
(104) 5,6-Dehydroprostaglandin $D_2$
(106) 16,17,18,19,20-Pentanor-15-cyclopentylprostaglandin $D_2$
(108) 16,17,18,19,20-Pentanor-15-cyclohexylprostaglandin $D_2$
(110) 17,20-Dimethylprostaglandin $D_2$
(112) 16,16-dimethylprostaglandin $D_2$
(114) 15-Methylprostaglandin $D_2$
(116) 17,18,19,20-Tetranor-16-cyclopentylprostaglandin $D_2$
(118) 17,18,19,20-Tetranor-16-cyclohexylprostaglandin $D_2$
(120) 18-Oxaprostaglandin $D_2$
(122) 17,17,20-Trimethylprostaglandin $D_2$
(124) Sodium
(126) Methyl ester of (100)
(128) Ethyl ester of (100)
(130) Sodium salt of (102)
(132) Methyl ester of (102)
(134) Ethyl ester of (102)

The process of this invention is characterized in that $PGD_2$ can be produced from 7-hydroxy $PGF_2\alpha$, which is obtained from 4-carboxycyclopentanone with the 2-stage process, used as the material compound, thus making the manufacturing process much shorter than the conventional ones.

A thiocarbonate composition expressed by the following formula (7),

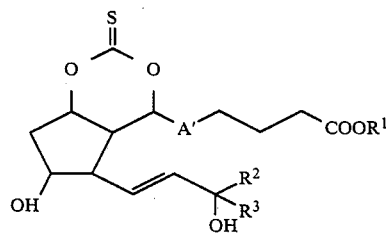

(7)

wherein $R^1$, $R^2$, $R^3$, and A are as defined hereinbefore, which is obtained from the thiocarbonate composition of formula (2) of the present invention by deprotection, is expected to display a pharmaceutical effect as a novel PG. It may be justly said that the present invention is characterized in providing not only a process for the production of $PGD_2$ much better than the conventional ones but also novel $PGF_2\alpha$ and a process for the production thereof.

The following Examples illustrate the present invention in detail.

REFERENTIAL EXAMPLE 1

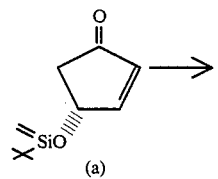

(a)

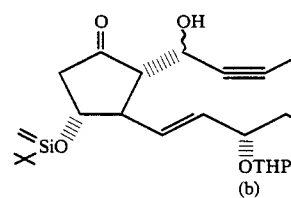

(b)

A solution of 664 mg of (E)-1-iodo-3-tetrahydropyranyloxy-1-octane in 10 ml of dry ether was prepared and t-butyl lithium was added thereto little by little at −95° C. The mixture was then warmed to −78° C. and stirred for 1.5 hours.

374 mg of cuprous iodide was placed in a 150 ml reaction tube. After the inside of the tube was dried under reduced pressure, argon was passed through the tube to displace the air. 40 ml of dry ether and 1.27 ml of tributylphosphine were added thereto and the mixture was stirred at room temperature (25.5° C.) to obtain a homogeneous solution. The solution was then cooled to −78° C. and the previously prepared vinyl lithium solution was poured there into in a single moment by use of a stainless steel tube, which was then washed down with 10 ml of ether. After the mixture was stirred for 10 minutes, 20 ml of an ether solution of (E)-1-iodo-3-tetrahydropyranyloxy-1-octane was allowed to trickle out of a stainless steel tube drop by drop along the inner walls of the reaction tube taking 40 minutes while cooling. The mixture was stirred for 10 minutes and the reaction tube was then cooled to −95° C. 15 ml of ether solution containing 309 mg of 6-carbomethoxyhexynal dissolved therein was added slowly dropwise with a stainless steel tube, which was washed thereafter with 5 ml of ether. After the mixture was stirred for 10 minutes, 40 ml saturated aqueous solution of ammonium acetate was added and the mixture was shaken vigorously. After the aqueous layer was separated from the organic layer, the aqueous solution was extracted with two 20 ml portions of ether. The extract and the organic layer were put together and were washed thoroughly with a mixed solution consisting of 2 ml of DMSO, 10 ml of benzene, and 40 ml of water to have the copper compound removed. The obtained reaction product was dried over anhydrous sodium sulfate, concentrated under reduced pressure, and put to column chromatography at a low temperature (0° C.) (100 g of 6% water containing silica gel manuf. by Merck+10 g of florizil; ethyl acetate-hexane-benzene (1:6:1)→ethylacetate-hexane (1:3)).

The chromatography gave 670.2 mg (60% yield) of 7-α,β-hydroxy-Δ⁵-PGE₂ methyl ester 11-t-butyldilyl, 15-tetrahydropyranyl ether (b) as a final product.

TLC: Rf=0.45, 0.41 (ethyl acetate-hexane=1:2)
Optical rotation:

| 7α-OH body: $[\alpha]^{25}D^5 =$ | −80.2° (CO.50, MeOH) |
|---|---|
| 7β-OH body: $[\alpha]^{25}D^5 =$ | −26.2° (CO.185, MeOH) |

7α-OH body
IR(CHCl₃): 3720-3000, 1735 cm⁻¹
¹HNMR(CDCl₃, 90 MHz, ppm) δ: 0.0-0.1 (m, 6, SiCH₂×2), 0.7-1.1 (m, 12, SiC(CH₃)₃, CH₃), 1.1-3.2 (m, 25, CH₂C=O×2, CH₂×9, CH×2, OH), 3.3-4.8 (m, 9, OCH₃, CHO×3, CH₂O, OCHO), 5.51 (m, 2, vinyl)

7β-OH body
IR(CHCl₃): 3700-3000, 1735 cm⁻¹
¹HNMR(CDCl₂, 90 MHz, ppm) δ: 0.0-0.1 (m, 6, SiCH₃×2), 0.7-1.1 (m, 12, SiC(CH₃)₃, CH₃), 1.1-3.1 (m, 25, CH₂C=O×2, CH₂×9, CH×2, OH), 3.4-4.2 (m, 8, OCH₃, CHO×3, CH₂O), 4.68 (m, 1, OCHO), 5.57 (m, 2, vinyl)

REFERENTIAL EXAMPLE 2

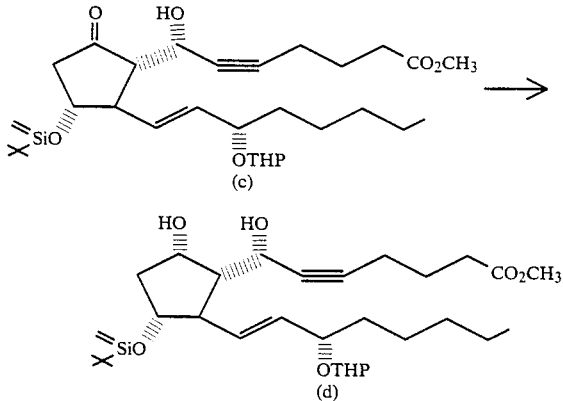

A solution of a ketone body (c) (293.2 mg, 5.07×10⁻⁴ mol) in 15 ml of methanol was prepared and 191.6 mg of NaBH₄ was added to the solution with stirring at 0° C. When the stirring at 0° C. for 15 minutes was over, the reaction solution was poured into 15 ml of a saturated aqueous solution of NH₄Cl with stirring at 0° C. After the liberation of bubbles ceased, the reaction solution was extracted three times with 10 ml of ethyl acetate. The extract, together with the organic layer, was dried over Na₂SO₄ and further concentrated under reduced pressure. The residue was subjected to column chromatography on silica gel (30 g of silica gel manuf. by Merck; ethyl acetate:hexane—1:3) to obtain 126 mg of 9α-OH body (d) (54% yield) as a final product.

TLC: Rf=0.60 (ethyl acetate-hexane=1:1)
$[\alpha]_D^{26}$= −20.7° (C0.663, CH₃OH)
IR(CHCl₃): 3740-3200, 1730 cm⁻¹
¹HNMR(CDCl₃, 70 MHz, ppm) δ: 0.0-0.1 (m, 6, SiCH₃×2), 0.7-1.0 (m, 12, C-CH₃×4), 1.0-3.3 (m, 26, CH₂C=O, CH₂×10, CH×2, OH×2), 3.3-4.8 (m, 10, OCH₃, CHO×4, CH₂O, OCHO), 5.51 (m, 2, vinyl)

REFERENTIAL EXAMPLE 3

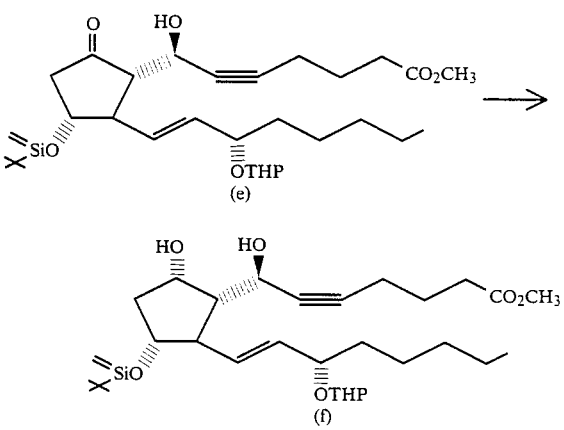

A ketone body (e) (121.7 mg, 2.10×10⁻⁴ mol) was dissolved in 8 ml of methanol and 79.5 mg of NaBH₄ was added thereto with a single rapid motion at 0° C. with stirring. After the mixture was stirred at 0° C. for 10 minutes, the reaction solution was poured into 8 ml of a saturated aqueous solution of HH₄Cl at 0° C. with stirring. After the bubbles ceased to rise any more, the reaction solution was extracted with three 10 ml portions of ethyl acetate Both the extract and the organic layer were dried all together over Na₂SO₄ and concentrated under reduced pressure. The residue was subjected to column chromatography on silica gel (12 g of Merck's silica gel; ethyl acetate—hexane=1:3) to give 62.2 mg (51% yield) of 9α-OH body (f) as a final product.

TLC: Rf=0.62 (ethyl acetate-hexane=1:1)
$[\alpha]_D^{26}$= −38.4° (C0.498, CH₃OH)
IR(CHCl₃): 3720-3300, 1730 cm⁻¹
¹HNMR(CDCl₃, 90 MHz, ppm) δ: 0.0-0.1 (m, 6, SiCH₃×2), 0.7-1.1 (m, 12, C-CH₃×4), 1.1-3.0 (m, 26, CH₃C≡), CH₂×10, CHO×2, CH₂O), 4.3-4.7 (m, 3, CHO×2, OCHO), 5.3-5.6 (m, 2, vinyl)

EXAMPLE 1

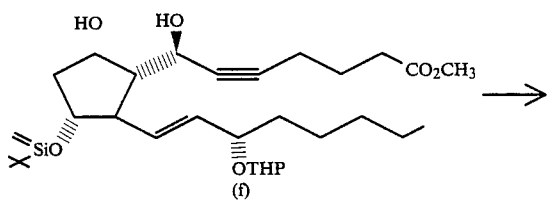
(f)

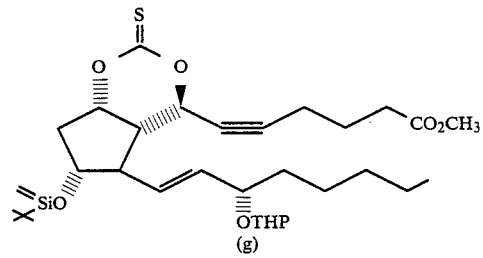
(g)

In a stream of argon, 57.6 mg of 9α-OH body (f), 26.5 mg of thiocarbonyldiimidazole, and 36.4 mg of 4-dimethylaminopyridine were placed in a 10 ml test tube and they were dissolved in 3 ml of dry acetonitrile. The solution was stirred at room temperature for 12 hours. After the reaction solution was diluted with 7 ml of methylene chloride, the dilution was thoroughly shaken together with a saturated aqueous solution of ammonium chloride. When the solution is separated into an aqueous layer and an organic layer, the aqueous layer was extracted with two 10 ml portions of methylene chloride. The resulting extract and the organic layer were mixed together and washed with 10 ml of saturated saline solution. The washed mixture was dried over anhydrous sodium sulfate, concentrated under reduced pressure, and subjected to column chromatography over silica gel (5 g of silica gel manuf. by Merck; ethyl acetate-hexane-benzene=1:5:1), thus giving 56.7 mg of thiocarbonate body (g) (92% yield) as a final product.

TLC: Rf=0.49 (ethyl acetate-hexane=1:2)
$[\alpha]_D^{26} = 7.66°$ (C0.3185, $CH_3OH$)
IR($CHCl_3$): 1730 $cm^{-1}$
$^1HNMR(CDCl_3)$, 90 MHz, ppm) δ: 0.04 (s, 6, $SiCH_3 \times 2$), 0.7–1.1 (m, 12, $SiC(CH_3)_3$, $CH_3$), 1.1–2.8 (m, 24, $CH_2C=O$, CH ×10, CH×2), 3.3–4.2 (m, 7, $OCH_3$, CHO×2, $CH_2O$), 4.63 (m, 1, OCHO), 4.9–5.1 (m, 2, CHO×2), 5.4–5.6 (m, 2H, vinyl)

EXAMPLE 2

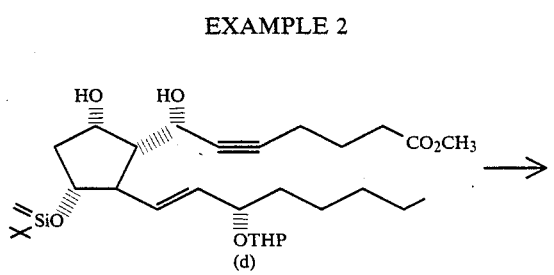
(d)

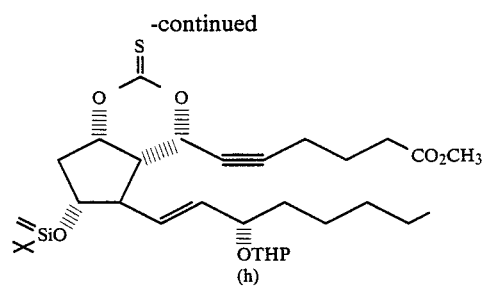
(h)

44.7 mg of 9α-OH body (d), 20.6 mg of thiocarbonyldiimidazole, and 28.2 mg of 4-dimethylaminopyridine were put in a 10 ml test tube while argon was kept streaming thereinto. The content was dissolved in 2.5 ml of dry acetonitrile and the solution was stirred for 14 hours at room temperature. After the reaction solution was diluted with 10 ml of methylene chloride, the dilution was thoroughly shaken together with a saturated aqueous solution of ammonium chloride. After the separation of the mixture into an aqueous layer and an organic layer was completed, the aqueous layer was extracted with two 10 ml portions of methylene chloride. The extract and the organic layer was washed all together and washed with 10 ml of saturated saline solution. After the washed mixture was dried over anhydrous sodium sulfate, it was concentrated under reduced pressure and subjected to column chromatography over silica gel (4 g of silica gel manuf. by Merck; ethyl acetate-hexane-benzene=1:5:1) to give 40.5 mg of a thiocarbonate body (h) (84% yield) as a final product.

TLC: Rf=0.49 (ethyl acetate-hexane=1:2)
$[\alpha]_D^{26} = +13.2°$ (C1.52, $CH_3OH$)
IR($CHCl_3$): 1733 $cm^{-1}$
$^1HNMR(CDCl_3)$, 90 MHz, ppm) δ: 0.06 (s, 6, $SiCH_3 \times 2$), 0.7–1.0 (m, 12, $SiC(CH_3)_3$, $CH_3$), 1.1–3.1 (m, 24, $CH_2C=O$, $CH_2 \times 10$, CH×2), 3.3–4.2 (m, 7, $OCH_3$, CHO×2, $CH_2O$), 4.65 (m, 1, OCHO), 4.87 (m, 1, CHO), 5.17 (m, 1, CHO), 5.4–5.6 (m, 2, vinyl)

EXAMPLE 3

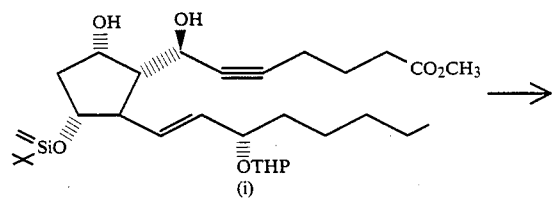
(i)

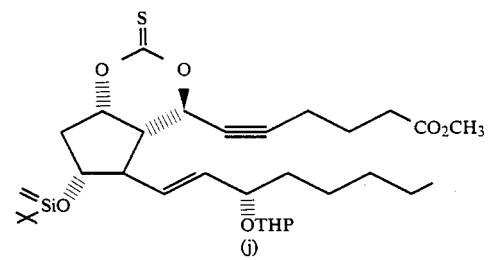
(j)

51.4 mg of a compound (i), 23.7 mg of thiocarbonyldiimidazole, and 32.5 mg of 4-dimethylaminopyridine were put in a 10 ml test tube under a stream of argon and dissolved in 3 ml of dry acetonitrile. The solution was stirred at room temperature for 15 hours. After the reaction solution was diluted with 7 ml of methylene chloride, the dilution was thoroughly shaken together with a saturated aqueous solution of ammonium chloride. When the solution was separated into an organic layer and an aqueous solution, the aqueous layer was extracted with two 10 ml portions of methylene chloride. The extract and the organic layer were put together and washed with 10 ml of saturated saline solution. The washed mixture was dried over anhydrous sodium sulfate, concentrated under reduced pressure, and subjected to column chromatography over silica gel (2.5 g of silica gel manuf. by Merck; ethyl acetate-hexane-benzene=1:5:1) to give 41.5 mg (75% yield) of a thiocarbonate body which presented the same spectrum data as the compound obtained in Example 1.

EXAMPLE 4

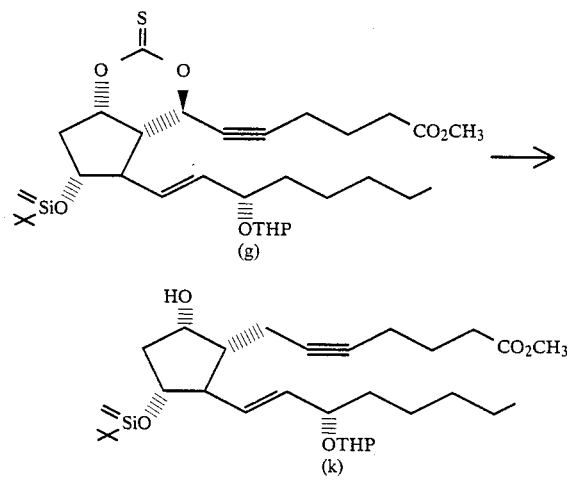

50.5 mg of a compound (g) was weighed into a 10 ml test tube and 0.5 ml of (n-Bu)$_3$SnH and 4 mg of bis-t-butylperoxide were further added thereto. The mixture was then stirred at 50° C. for 50 minutes in a stream of argon. After the temperature was lowered to a room temperature (26° C.), 1 ml of 1N CH$_3$ONa—CH$_3$OH and 1 ml of dry THF were added and the mixture was stirred for 13 hours at room temperature (26° C.). The reaction mixture was then diluted with 5 ml of THF and 5 ml of saturated aqueous solution of ammonium chloride and the mixture was shaken enough. After the addition of 5 ml of ethyl acetate, the mixture was again shaken thoroughly to have an aqueous layer separated from an organic layer. The aqueous layer was extracted with two 10 ml portions of ethyl acetate. The extract and the organic layer were dried together over anhydrous sodium sulfate, concentrated under reduced pressure, and subjected to column chromatography over silica gel (2.5 g of silica gel manuf. by Merck; ethyl acetate-hexane=1:6) to give 26.8 mg of Δ$^5$-PGF$_{2\alpha}$ body (k) (59% yield).

TLC: Rf=0.53 (ethyl acetate-hexane=1:2)

[α]$_D^{26}$ = −28.8 (C1.30, CH$_3$OH)

IR(CHCl$_3$): 3720-3300, 1730 cm$^{-1}$ $^1$HNMR(CDCl$_3$, 90 MHz, ppm) δ: 0.03 (s, 6, SiCH$_3$×2), 0.6-1.1 (m, 12, SiC(CH$_3$)$_3$, CH$_3$), 1.1-2.7 (m, 27, CH$_2$C≡C, CH$_2$×11, CH×2, OH), 3.3-4.4 (m, 8, OHC$_3$, CHO×3, CH$_2$O), 4.66 (m, 1, OCHO), 5.2-5.6 (m, 2, vinyl)

EXAMPLE 5

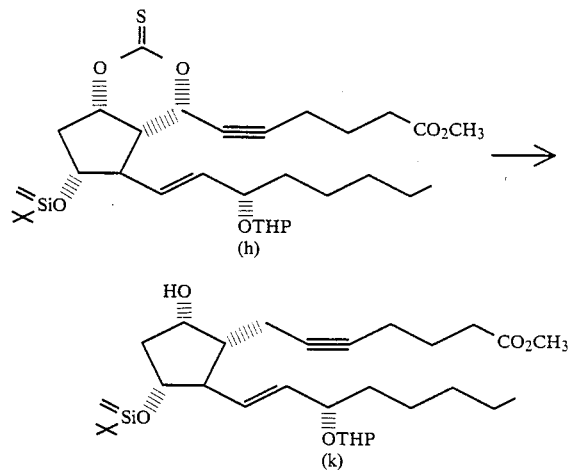

21.1 mg of a compound (h) was weighed into a 10 ml test tube and 0.5 ml of (n-Bu)$_3$SnH and 4 mg of bis-t-butylperoxide were added thereto. The content was stirred at 50° C. for 70 minutes in a stream of argon. The temperature was then lowered to a room temperature (27.5° C.) and 1 ml of 1N CH$_3$ONa—CH$_3$OH and 1 ml of dry THF were added. The mixture was stirred at room temperature (27.5° C.) for 2 hours. After the reaction mixture was diluted with 5 ml of THF, 5 ml of a saturated aqueous solution of ammonium chloride was added thereto and shaken thoroughly. 5 ml of ethyl acetate was added and shaken thoroughly again until the separation of an aqueous layer from an organic layer was completed. The aqueous layer was extracted twice, each time with 10 ml of ethyl acetate. The extract and the organic layer were put together, dried over anhydrous sodium sulfate, and subjected to column chromatography over silica gel (2 g of silica gel; ethyl acetate-hexane=1:6) to obtain 14.6 mg (76% yield) of Δ$^5$-PGF$_2$ body (k), which is the same product as obtained in Example 4.

EXAMPLE 6

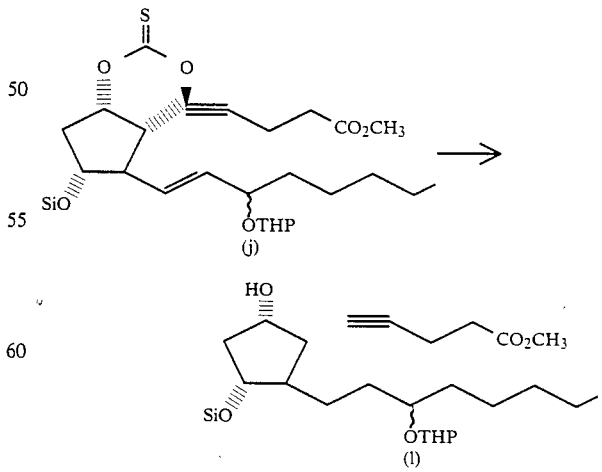

41.5 mg of a compound (j) was placed in a 5 ml test tube and 0.4 ml of (n-Bu)$_3$SnH and 4 mg of bis-t-butylperoxide were added thereto. The mixture was stirred in a stream of argon at 50° C. for 1.5 hours. After the temperature was lowered to a room temperature (20° C.), 1 ml of 1N CH₃ONa—CH₃OH and 1 ml of dry THF were added. The mixture was stirred at room temperature (20° C.) for 14.5 hours. Then, 10 ml of a saturated aqueous solution of NH₄Cl was added and the mixture was thoroughly shaken. 10 ml of ethyl acetate was added and the admixture was again shaken thoroughly to cause the separation of an organic layer from an aqueous layer. The aqueous layer was extracted two times with 10 ml of ethyl acetate each time. The extract and the organic layer were dried together over anhydrous sodium sulfate, concentrated under reduced pressure, and subjected to column chromatography over silica gel (2.5 g of silica gel manuf. by Merck; ethylacetate-hexane=1:6) to obtain 19.5 mg (52% yield) of $\Delta^5$-PGF₂α body (l). This product presented the same spectrum data as shown in Example 4.

EXAMPLE 7

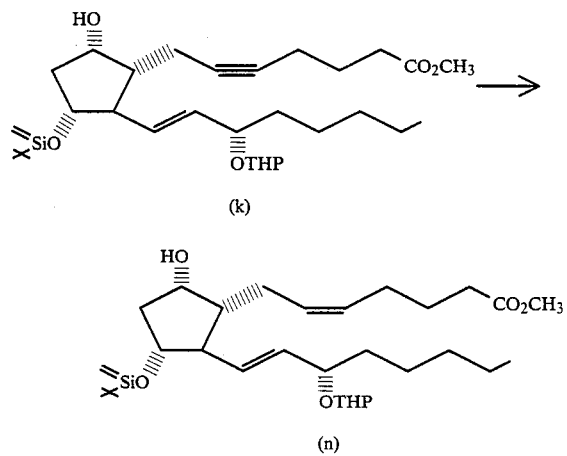

21.2 ml of $\Delta^5$-PGF₂ body (k) was placed in a messflask and was dissolved in 1 ml of cyclohexane, 1 ml of benzene, and 0.02 ml of cyclohexene. Thereafter, 24.1 mg of Lindlar catalyst was added to the solution and the air in the flask was replaced with hydrogen. The content was then stirred at 26° C. for 13 hours under hydrogen pressure exerted by a hydrogen balloon. The reaction solution was passed through a column of Celite to remove palladium therefrom and was then washed thorough with ethyl acetate. The filtrate was concentrated under reduced pressure and subjected to column chromatography over silica gel (2.4 g of silica gel manuf. by Merck; ethyl acetate-hexane=1:12) to obtain 20.3 mg (96% yield) of PGF₂α body (m) as a final product.

TLC: Rf=0.46 (ethyl acetate-hexane=1:4)

$[\alpha]_D^{27} = -20.6°$

IR(CHCl₃): 3740–3300, 1730 cm⁻¹

¹HNMR(CDCl₃, 90 MHz, ppm) δ: 0.04 (s, 6, SiCH₃×2), 0.7–1.0 (m, 12, SiC(CH₂)₂, CH₃), 1.0–2.7 (m, 27, CH₂O=O, CH₂×11, CH×2, OH), 3.3–4.2 (m, 8, OCH₃, CHO×3, CH₂O), 4.67 (m, 1, OCHO), 5.1–5.6 (m, 4, vinyl)

EXAMPLE 8

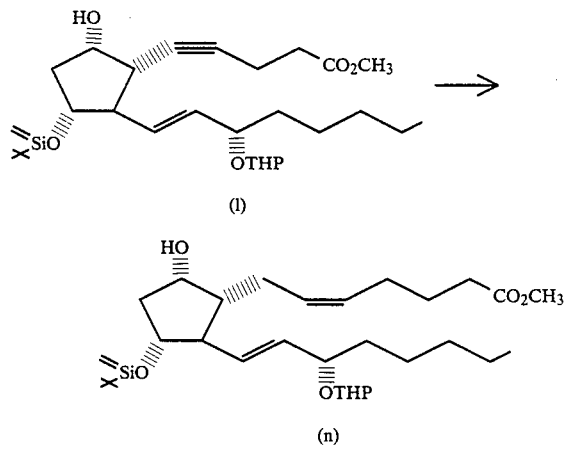

10.8 mg of $\Delta^5$-PGF₂α body (l) was weighed into a 10 ml messflask and 0.7 ml of cyclohexane and 0.7 ml of benzene were added thereto. The air in the messflask was replaced with hydrogen and the content was stirred at 22° C. for 14 hours under hydrogen pressure exerted by a hydrogen balloon. The reaction solution was passed through a column of Celite to remove palladium from it and washed thoroughly with ethyl acetate. The filtrate was concentrated under reduced pressure and subjected to column chromatography over silica gel (1 g of silica gel manuf. by Merck; ethyl acetate-hexane-benzene=1:8:1) to give 10.3 mg (95% yield) of PGF₂α body (n). The same spectrum data as those of a compound (m) of Example 7 were recorded.

EXAMPLE 9

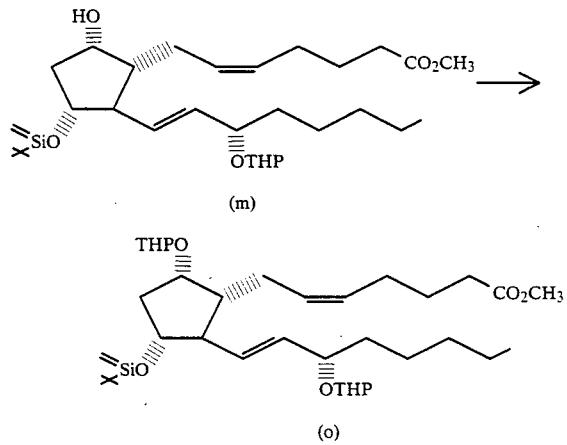

PGF₂α body (m) was placed in a 5 ml test tube and 0.2 ml of dry CH₂Cl₂ was added thereto. While cooling the test tube on an ice bath, 6.0 mg of 2,3-dihydropyran and further 4.5 mg of pyridine salt-p-toluenesulfonate (PPTS) were added. The mixture was stirred first at 0° C. for 10 minutes and then at a6° C. for 3 hours. After the reaction solution was diluted with 5 ml of CH₂Cl₂, 5 ml of a saturated saline solution was added and the mixture was shaken thoroughly to remove PPTS from there. The aqueous layer was extracted twice with 5 ml of CH₂Cl₂ each time. The extract and the organic layer were dried together over anhydrous sodium sulfate, filtered through a cotton ward, concentrated to have the solvent removed therefrom, and subjected to column chromatography over silica gel (2 g of silica gel manuf. by Merck; ethyl acetate-hexane=1:15) to obtain 23.2 mg (99.5% yield) of a protected PGF$_2\alpha$ body (o).

TLC: Rf=0.58 (ethyl acetate-hexane=1:4)

$[\alpha]_D^{27}$=−8.3° (C, 0.72 CH$_3$OH)

$^1$HNMR(CDCl$_3$, 90 MHz, ppm) δ: 0.007 (s,6, SiCH$_3$×2), 0.7-1.0 (m, 12, SiC(CH$_3$)$_3$, CH$_3$), 1.0-2.6 (m, 32, CH$_2$C=O, CH$_2$×14, CH×2), 3.3-4.2 (m, 10, OCH×3, CH$_2$O×2), 4.5-5.0 (m, 2, OCHO), 5.2-5.6 (m, 4, vinyl)

EXAMPLE 10

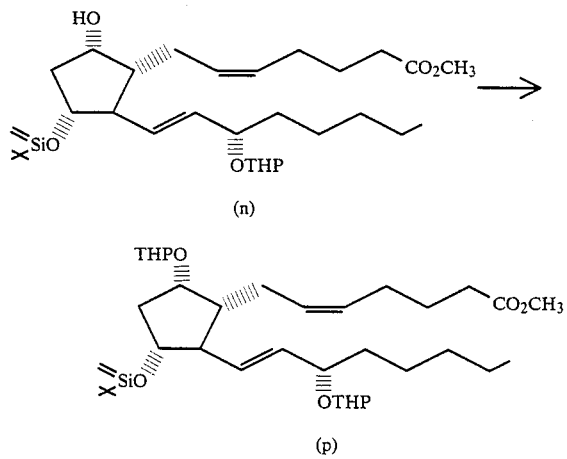

PGF$_2\alpha$ body (n) was placed in a 5 ml test tube and 0.1 ml of dry CH$_2$Cl$_2$ was added thereto. While cooling the test tube on an ice bath, 3.1 mg of 2,3-dihydropyran was first added and then 0.4 mg of PPTS was added. The mixture was stirred first at 0° C. for 10 minutes and then at 24° C. for 4 hours. After the reaction mixture was diluted with 5 ml of CH$_2$Cl$_2$, 5 ml of saturated saline solution was added and the mixture was shaken thoroughly to transfer PPTS to the aqueous layer. The aqueous layer was extracted twice with two 5 ml portions of CH$_2$Cl$_2$. The extract and the organic layer were dried together over anhydrous sodium sulfate and filtered through a cotton ward. After the removal of the solvent and the concentration were over, the filtrate was subjected to column chromatography over silica gel (1 g of silica gel manuf. by Merck; ethyl acetate-hexane=1:15) to obtain 10.3 mg (87.% yield) of protected PGF$_2\alpha$ body (p) as a final product.

The product presented the same spectrum data as those of a compound (o) of Example 9.

EXAMPLE 11

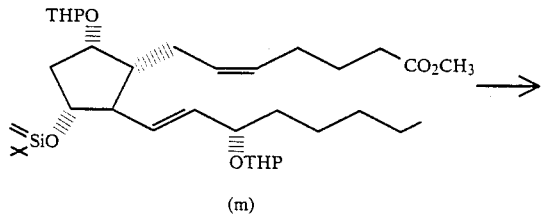

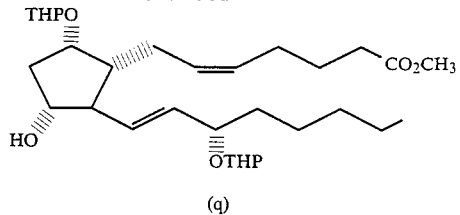

18.4 mg of PGF$_2\alpha$ body (m) was placed in a 5 m test tube and dissolved in 0.4 ml of THF. 0.42 ml of tetra-n-butylammonium fluoride (n-Bu$_4$NF) (1M/THF)was added to the solution and the mixture was stirred at room temperature (26° C.) for 3 hours. After the reaction mixture was diluted with 5 ml of THF, 5 ml of saturated saline solution was added thereto and thoroughly shaken. An aqueous layer was separated from an organic layer and the aqueous layer was extracted with two 10 ml portions of ethyl acetate. The extract and the organic layer were concentrated and subjected to column chromatography over silica gel (1.8 g of silica gel manuf. by Merck; ethyl acetate-hexane=1:3) to obtain 14.4 g of PGF$_2\alpha$ body (q) with its 11-position remaining free (95% yield).

TLC: Rf=0.14 (ethyl acetate-hexane=1:2)

$[\alpha]_D^{28}$=−6.76° (C0.72, CH$_3$OH)

IR(CHCl$_3$): 3700-3300, 1730 cm$^{-1}$ $^1$HNMR(CDCl$_3$, 9- MHz, ppm) δ: 0.88 (t, 3, J=6.0 Hz, CH$_3$), 1.0-2.6 (m, 33, CH$_2$×14, CH×2, OH), 3.3-4.3 (m, 10, OCH$_3$, CHO×3, CH$_2$O×2), 4.5-4.8 (m, 2. OCHO), 5.1-5.6 (m, 4, vinyl)

EXAMPLE 12

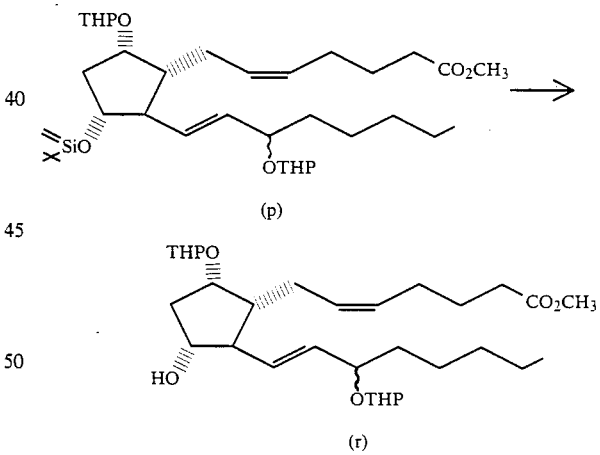

After 10.3 mg of PGF$_2\alpha$ body (p) placed in a 5 ml test tube was dissolved in 0.25 ml of THF, 0.24 ml of n-Bu$_4$NF (1M/THF) was added to the solution and the mixture was stirred at room temperature (24° C.) for 2 hours. The reaction mixture was diluted with 5 ml of THF and 5 ml of saturated saline solution was added. The mixture was shaken thoroughly and 5 ml of ethyl acetate was added for extracting purpose. After the separation between an aqueous layer and an organic layer was completed, the aqueous layer was extracted with two 10 ml portions of ethyl acetate. The extract and the organic layer were concentrated together and subjected to column chromatography over silica gel (1 g of silica gel; ethyl acetate-hexane=1:3) to obtain 7.1 mg (84% yield) of a compound (r) having the same spectrum data as the compound (q) of Example 11.

EXAMPLE 13

(q)

(s)

14 4 mg of PGF$_2\alpha$ body (q) was dissolved in 0.8 ml of acetone in a 5 ml test tube and 12.4 μl of Jones reactant (2.4M) was added to the solution dropwise with a syringe at −30° C. in a stream of argon. The mixture was stirred at −30° C. for 30 minutes and then diluted with 1 ml of ethyl acetate. After 1 ml of a saturated aqueous solution of sodium hydrogencarbonate was added, the mixture was agitated vigorously. When the color of the aqueous layer shaded into green, 10 ml of ethyl acetate and 10 ml of a saturated aqueous solution of sodium hydrogen-carbonate were further added and the mixture was agitated vigorously. The organic layer and the aqueous layer were extracted with two 10 ml portions of ethyl acetate. The extract and the organic layer were dried together over anhydrous sodium sulfate, concentrated under reduced pressure, and subjected to column chromatography over silica gel (1.4 g of silica gel manuf. by Merck; ethylacetate-hexane=1:3) to obtain 13.1 mg (91% yield) of PGD$_2$ body (s).

TLC: Rf=0.42 (ethyl acetate-hexane=1:2)

$[\alpha]_D^{27}$ = −7.23° (C0.575, CH$_3$OH)

IR(CHCl$_3$) 1740 cm$^{-1}$ $^1$HNMR(CDCl$_3$, 90 MHz, ppm) δ: 0.88 (t, 3, J=4.8 Hz, CH$_3$), 1.1–3.0 (m, 32, CH$_2$C=O×2, CHC=O, CH$_2$×13, CH×1), 3.3–4.8 (m, 11, OCH$_3$, CHO×2, CH$_2$O×2, OCHO×2), 5.3–5.6 (m, 4, vinyl)

EXAMPLE 14

(r)

(t)

7.1 mg of a compound (r) was weighed into a 5 ml test tube and dissolved in 0.4 ml of acetone. 6.1 μl of Jones reactant (2.4 M) was added to the solution drop by drop with a syringe at −30° C. in a stream of argon. After the mixture was stirred at −30° C. for 70 minutes, it was diluted with 1 ml of ethyl acetate and 1 mul of a saturated aqueous solution of sodium hydrogencarbonate and the mixture was agitated vigorously. When the aqueous layer took on a green color, another 10 ml of ethyl acetate and 10 ml of the saturated aqueous solution of sodium hydrogencarbonate were added, and the mixture was vigorously agitated. The organic layer and the aqueous layer were extracted twice with 10 ml of ethyl acetate respectively. The extract and the organic layer were dried together over anhydrous sodium sulfate, concentrated under reduced pressure, and subjected to column chromatography over silica gel (1 g of silica gel manuf. by Merck; ethyl acetate-hexane:1:3) to obtain 6.6 mg (94% yield) of a compound (t).

The product had the same spectrum data as the compound (s) of Example 13.

EXAMPLE 15

(s)

(u)

The PGD$_2$ body (s) obtained in Example 13 was dissolved in 2 ml of AcOH—H$_2$O—THF (3:1:1) and stirred first at 26° C. for 14 hours and then at 35° C. for 5 hours. After the removal of the solvent by use of a vacuum pump, the solution was azeotropically distilled three times with toluene. The concentrate was subjected to column chromatography over silica gel (1 g of silica gel manuf. by Merck; ethyl acetate-hexane=2:3) to obtain 7.0 mg of PGD$_2$ method ester (u) (88% yield).

TLC: Rf=0.17 (ethyl acetate-hexane =1:1)

$[\alpha]_D^{27}$ = +21.7° (C0.35, CH$_3$OH) (Document value +26.0°)

IR(CHCl$_3$): 3720–3230, 1740, 1730 cm$^{-1}$ $^1$HNMR(CDCl$_3$, 90 MHz, ppm) δ: 0.89 (t, 3, J=6.0 Hz, CH$_3$), 1.1–2.2 (m, 17, CH$_2$×7, CH×1, OH×2), 2.34 (t, 2, J-6.4 Hz, CH$_2$COOC), 2.43 (d, 2, J=2.9, $CH_2C=O$), 2.86 (dd, 1, J=11.6, 7, OHz, OHC=O), 3.68 (s, 3, $OCH_3$), 4.09 (m, 1, OHC), 4.49 (m, 1, CHO), 5.2–5.8 (m, 4, vinyl)

EXAMPLE 16

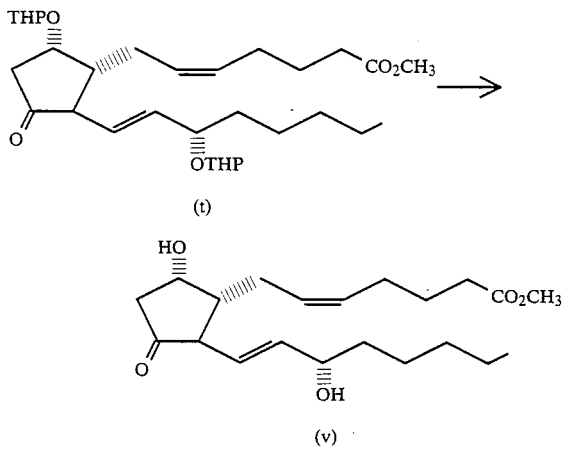

A solution of 6.4 mg ($1.2 \times 10^{-5}$ ml) of a compound (t) dissolved in 1 ml of $AcOH-H_2O-THF$ (3:1:1) was stirred at 40° C. for 7.8 hours. After the removal of the solvent by a vacuum pump, the reaction product was subjected to azeotropic distillation three times with toluene and the concentrate was subjected to column chromatography our silica gel (1 g of silica gel manuf. by Merck; ethyl acetate-hexane=1:2→2:3→1:0) to obtain 3.3 mg of a product (v) (75% yield). As seen from its spectrum data including TLC: Rf=0.69, 0.58 (ethyl acetate-cyclohexane-THF), this product was found to be a mixture of $PGD_2$ methyl ester and 15-epimer.

INDUSTRIAL APPLICATION

The present invention relates to a process for producing pharmacologically useful $PGD_2$ compounds at an extremely high efficiency and accordingly an industrially advantageous method of producing $PGD_2$ is provided by this invention.

What is claimed is:

1. A process for the production of prostaglandin $D_2$ represented by the following formula (6)

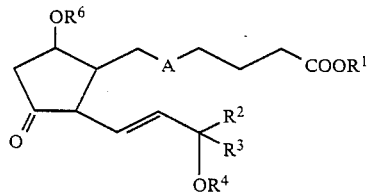

wherein
A indicates a single bond, a double bond, or a triple bond,
$R^2$ and $R^3$ are the same or different from each other, each representing a hydrogen atom, a $C_1 \sim C_{10}$ alkyl group which may be substituted or may not be substituted, or a cycloalkyl group which may be substituted or may not be substituted,
$R^1$ indicates a hydrogen atom, a $C_1 \sim C_{10}$ alkyl group, a phenyl group which may be substituted or may not be substituted, an alicyclic group which may be substituted or may not be substituted, a phenyl ($C_1 \sim C_2$) alkyl group which may be substituted or may not be substituted, a tri($C_1 \sim C_7$) hydrocarbon silyl group, or one equivalent of cation,
$R^4$ and $R^6$ are the same or different from each other, each representing a hydrogen atom or a group which forms an acetal bond together with an oxygen atom of a hydroxyl group,
and wherein the substituents for the alkyl group, phenyl group, phenyl alkyl group, or alicyclic group are selected from the group consisting of a halogen atom, a hydroxy group, a $C_2 \sim C_7$ acyloxy group, a $C_1 \sim C_7$ alkyl group which may be substituted with a halogen atom, a $C_1 \sim C_4$ alkoxy group which may be substituted with a halogen atom, a nitrile group, a carboxyl group, and a ($C_1 \sim C_6$) alkoxycarbonyl group,
comprising treating 7-hydroxy prostaglandin $F_{2\alpha}$ expressed by the following formula (1)

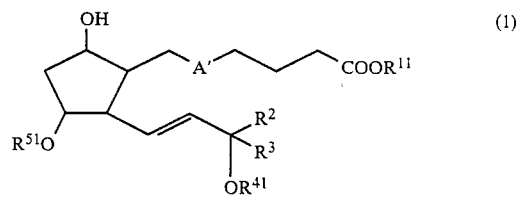

wherein
$R^{11}$ indicates a $C_1 \sim C_{10}$ alkyl group, a phenyl group which may be substituted or may not be substituted, an alicyclic group which may be substituted or may not be substituted, a phenyl ($C_1 \sim C_2$) alkyl group, or a tri($C_1 \sim C_7$) hydrocarbon silyl group, and wherein the substituents for the alkyl group, the phenyl group, the alicyclic group or the phenyl alkyl group are selected from the group consisting of a halogen atom, a hydroxy group, a $C_2 \sim C_7$ acyloxy group, a $C_1 \sim C_7$ alkyl group which may be substituted with a halogen atom, a $C_1 \sim C_4$ alkoxy group which may be substituted with a halogen atom, a nitrile group, a carboxyl group, and a ($C_1 \sim C_6$) alkoxycarbonyl group,
$R^2$ and $R^3$ are as defined hereinabove,
$R^{41}$ indicates a group which forms an acetal bond together with an oxygen atom of a hydroxyl group,
$R^{51}$ indicates a tri($C_1 \sim C_7$) hydrocarbon silyl group,
A' indicates a triple bond or a double bond,
with thiocarbonyl diimidazole or thiocarbonyl diimidazole which is substituted by $C_1$ to $C_6$ alkyl groups such as naphthyl and ethyl; $C_1$ to $C_6$ alkoxy groups such as methoxy, ethoxy, and propoxy; or halogen atoms such as fluorine and chlorine to obtain a thiocarbonate body expressed by the following formula (2)

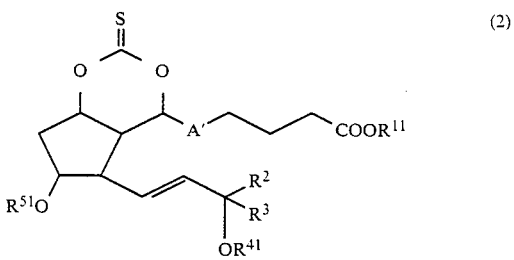

wherein $R^{11}$, $R^2$, $R^3$, $R^{41}$, $R^{51}$, and $A^1$ are as defined hereinabove, which is then subjected to the reaction to deoxidize the hydroxyl group at the 7-position, followed by the reduction of the triple bond or a double bond at the 5-position if needed to obtain a reduced type of compound, to give prostaglandin $F_{2\alpha}$ expressed by the following formula (3)

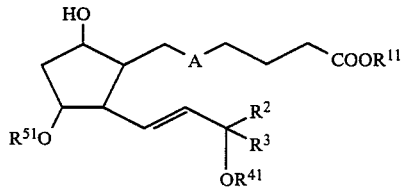
(3)

wherein A indicates a single bond, a double bond, or a triple bond; and $R_{11}$, $R^2$, $R^3$, $R^{41}$, and $R^{51}$ are as defined hereinabove,
whose hydroxyl group at the 9-position is protected thereafter with a group which forms an acetal bond together with an oxygen atom of the hydroxyl group, to obtain protected prostaglandin $F_{2\alpha}$ expressed by the following formula (4)

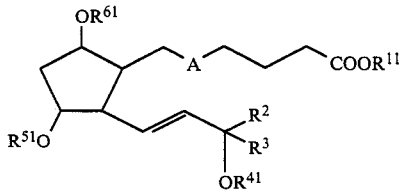
(4)

wherein $R^{61}$ indicates a group which forms an acetal bond together with an oxygen atom of the hydroxyl group; and $R^{11}$, $R^2$, $R^3$, $R^{41}$, $R^{51}$, and A are as defined hereinabove,
which is then subjected to the selective deprotection reaction of $R^{51}$, followed, if needed to obtain a reduced type of compound, by the reduction of the triple bond or the double bond at the 5-position, to obtain prostaglandin $F_{2\alpha}$ expressed by the following formula (5)

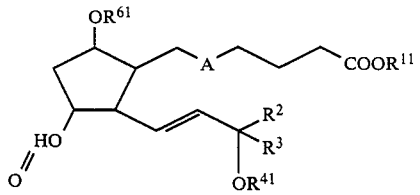
(5)

wherein $R^{11}$, $R^2$, $R^3$, $R^{41}$, $R^{51}$ and A are as defined hereinabove,
which is then subjected to the oxidation reaction, followed, if necessary to obtain a reduced type of compound, by the reduction of the triple bond or the double bond at the 5-position, deprotection, hydrolysis and/or salt-forming reaction.

2. A process according to claim 1 for producing prostaglandin $D_2$, wherein said reaction of deoxidizing the hydroxyl group at the 7-position involves a treatment with a compound of formula $(R^7)_3SnH$ (where $R^7$ indicates a $C_1 \sim C_{10}$ alkyl group or a phenyl group) and then another treatment with a base.

3. A process according to claim 1 for producing prostaglandin $D_2$, wherein said selective deprotection reaction is carried out by use of tetra-n-butyl-ammonium fluoride.

4. A process according to any one of claims 1 to 3 for producing prostaglandins $D_2$, wherein said treatment with thiocarbonyl diimidazole or its analog is carried out in the presence of amines.

5. A process according to claim 2 for producing prostaglandin $D_2$, wherein said selective deprotection reaction is carried out by use of tetra-n-butyl-ammonium fluoride.

6. A process according to claim 1 for producing prostaglandin $D_2$, wherein said oxidation reaction is carried out by use of an oxidizing agent of chromic acid system.

7. A process according to claim 2 for producing prostaglandin $D_2$, wherein said oxidation reaction is carried out by use of an oxidizing agent of chromic acid system.

8. A process according to claim 3 for producing prostaglandin $D_2$, wherein said oxidation reaction is carried out by use of an oxidizing agent of chromic acid system.

9. A process according to claim 5 for producing prostaglandin $D_2$, wherein said oxidation reaction is carried out by use of an oxidizing agent of chromic acid system.

* * * * *